United States Patent [19]

Bushell et al.

[11] 4,296,029
[45] Oct. 20, 1981

[54] PROCESS FOR PREPARING HEXAHYDROAZEPINE, PIPERIDINE AND PYRROLIDINE DERIVATIVES

[75] Inventors: Brian J. Bushell, Portsmouth; John F. Cavalla, Isleworth; Robin G. Shepherd, Burnham; Alan C. White, Windsor, all of England

[73] Assignee: John Wyeth & Brother Limited, Maidenhead, England

[21] Appl. No.: 161,992

[22] Filed: Jun. 23, 1980

[30] Foreign Application Priority Data

Jul. 3, 1979 [GB] United Kingdom ............... 23123/79

[51] Int. Cl.³ .......................................... C07D 223/10
[52] U.S. Cl. .................. 260/239.3 R; 260/326.5 FL; 260/326.8; 546/216; 546/221; 546/236; 546/240
[58] Field of Search ............... 260/239.3 R, 326.5 FL; 546/216

[56] References Cited

U.S. PATENT DOCUMENTS 3,729,465  4/1973  Cavalla et al. ............... 260/239.3 R
4,197,239  4/1980  Cavalla et al. ............... 260/239.3 R
4,197,241  4/1980  Cavalla et al. ............... 260/239.3 R

FOREIGN PATENT DOCUMENTS 3253  8/1979  European Pat. Off. ...... 260/239.3 R
1285025  8/1972  United Kingdom ......... 260/239.3 R

OTHER PUBLICATIONS

Scardiglia and Roberts "Tetrahedron", vol. 3, pp. 197-208, (1958).
Duong et al. "Australian J. of Chemistry", (1976), vol. 29, pp. 2651-2665.
March "Advanced Organic Chemistry", McGraw-Hill, (1968), pp. 492-494.
Morrison et al. "Organic Chemistry", Third Edition, Allyn and Bacon, (1973), pp. 835-841.

Primary Examiner—Robert T. Bond
Attorney, Agent, or Firm—George Tarnowski

[57] ABSTRACT

2-Oxo-hexahydroazepine, -piperidine or pyrrolidines of formula

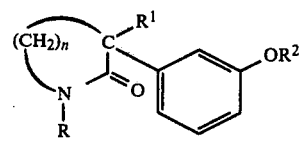

wherein n is 2,3 or 4, R is hydrogen, lower alkyl, aryl(lower)alkyl, loweralkenylmethyl or cycloalkylmethyl, $R^1$ is hydrogen or lower alkyl and $R^2$ is hydrogen, lower alkyl or aryl(lower)alkyl are prepared by a novel process involving reaction of an anion of a lactam of formula

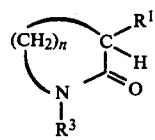

where $R^3$ is lower alkyl, aryl(lower)alkyl, trialkyl-, triaryl- or triarylalkyl-silyl with a benzyne of formula

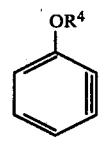

where $R^4$ is lower alkyl, aryl(lower)alkyl or trialkyl-, triaryl- or triarylalkyl-silyl. The products are useful as intermediates for preparing pharmacologically active 2-unsubstituted -hexahydroazepine, -piperidine and pyrrolidine derivatives.

15 Claims, No Drawings

PROCESS FOR PREPARING HEXAHYDROAZEPINE, PIPERIDINE AND PYRROLIDINE DERIVATIVES

This invention relates to hexahydroazepine, piperidine and pyrrolidine derivatives. More particularly the invention relates to a novel process for preparing 2-oxo-hexahydroazepine, -piperidine and -pyrrolidine derivatives.

The 2-oxo-hexahydroazepine, -piperidine and pyrrolidine derivatives prepared by the novel process of the present invention have the general formula (I)

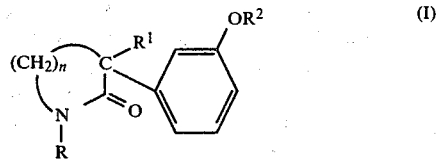

wherein n is 2,3 or 4, R is hydrogen, lower alkyl aryl(-lower)alkyl, loweralkenylmethyl or cycloalkylmethyl, $R^1$ is hydrogen or lower alkyl and $R^2$ is hydrogen, lower alkyl or aryl(lower)alkyl.

These derivatives may be converted to the pharmacologically active 2-unsubstituted-hexahydroazepine, -piperidine and pyrrolidine derivatives of general formula (II)

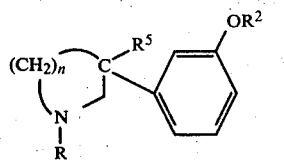

where n, R and $R^2$ have the meanings given above and $R^5$ is lower alkyl. Compounds of general formula (I) in which $R^1$ is hydrogen may be C-alkylated (e.g. by reaction with an alkyl halide in presence of a strong base) to compounds of general formula (I) in which $R^1$ is lower alkyl. Compounds of general formula (I) in which $R^1$ is lower alkyl may be reduced (e.g. with a hydride transfer agent such as lithium aluminium hydride) to the compounds of general formula II. Compounds of general formula (II) in which $R^2$ is lower alkyl or aryl(-lower) alkyl may be ether cleaved (e.g. with hydrogen bromide or boron tribromide) to compounds in which $R^2$ is hydrogen. The use of the compounds of formula (II) and their preparation from compounds of formula (I) is further exemplified in, for example, U.K. Patent Specification No. 1,285,025 and European Patent Application Publication No. 0 003 253. The present invention provides a novel process for preparing the intermediates of general formula (I).

According to the present invention there is provided a process for preparing a compound of general formula (I) which comprises reacting an anion of a lactam derivative of general formula (III)

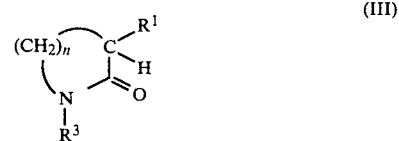

where n and $R^1$ are as defined above and $R^3$ is lower alkyl, aryl(lower)alkyl, trialkyl-, triaryl- or triarylalkyl-silyl, loweralkenymethyl or cycloalkylmethyl with a benzyne of general formula (IV)

where $R^4$ is lower alkyl, aryl(lower)alkyl or trialkyl-, triaryl- or triarylalkyl-silyl to give an anion of the compound of general formula I where $R^1$ is lower alkyl or a dianion of the compound of general formula I where $R^1$ is hydrogen (if desired reacting the dianion where $R^1$ is hydrogen with a (lower)alkylating agent to give an anion of the compound of general formula I where $R^1$ is lower alkyl) and protonating the anion or dianion of the compound of general formula I to give a compound of general formula I.

The term "lower" as used herein means that the radical referred to contains 1 to 6 carbon atoms. The radical preferably contains 1 to 4 carbon atoms. For example when R or $R^2$ is lower alkyl, the radical may be, for example, methyl, ethyl, propyl or butyl. Similarly $R^1$ may be, for example, methyl, ethyl, propyl or butyl. When R, $R^2$, $R^3$ or $R^4$ is aryl(lower)alkyl, the radical is preferably a phenyl(lower)alkyl radical such as phenethyl or benzyl; the phenyl group may be subtituted by, for example, substituents such as alkyl or alkoxy. When R or $R^3$ is loweralkenymethyl the radical is preferably allyl. When R or $R^3$ is cycloalkylmethyl the radical is preferably cyclopropylmethyl or cyclobutylmethyl.

The anion of the lactam of general formula (III) may be formed in situ by reacting the lactam with an alkyl lithium (e.g. tertiary butyl lithium) or with a compound of general formula MA where M is sodium, potassium or lithium and A is a secondary amine radical. The compound MA is a metal amide and is itself preferably formed in situ by reacting a metal compound $MR^5$ (where M is sodium, potassium or lithium and $R^5$ is alkyl, aryl or aralkyl) with a secondary amine. The secondary amine may be a dialkylamine, e.g. diethylamine, di-isopropylamine, di-tertiarybutylamine, di-cyclohexylamine, t-butyl-cyclohexylamine, N-t-amyl-N-t-butylamine, N-isopropyl-N-cyclohexylamine or N-(1'-ethylcyclohexyl)-1,1,3,3-tetramethylbutylamine or a cyclic compound, e.g. piperidine or 2,2,6,6-tetramethylpiperidine. Preferably the anion of the lactam is formed by reacting the lactam with lithium 2,2,6,6-tetramethylpiperidide (which may be prepared in situ from 2,2,6,6-tetramethylpiperidine and, for example, butyl lithium).

The benzyne of general formula (IV) is formed in situ by, for example, reaction of a substituted halobenzene of general formula (V)

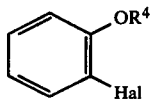

(V)

where $R^4$ is as defined above and Hal is chlorine, bromine or iodine (preferably chlorine) with a strong base, such as an agent mentioned above for the formation of the anion of the lactam of formula (IV). Preferably the strong base is lithium 2,2,6,6-tetramethylpiperidide (which as mentioned above may be formed in situ).

In an especially preferred process the formation of the anion of the lactam (III) and the formation of the benzyne is carried out in the same reaction vessel to give the anion or dianion of the compound (I). For example, a base such as lithium 2,2,6,6-tetramethylpiperidide (formed in situ) may be reacted with a lactam of formula (III) to give the anion of the lactam and further lithium 2,2,6,6-tetramethylpiperidide may be generated in situ (by for example adding an alkyl lithium such as butyl lithium) and the substituted halobenzene (V) then added. The addition of the required quantity of substituted halobenzene (V), together with the further generation of the lithium 2,2,6,6-tetramethylpiperidide or other base, may be carried out in two or more separate additions.

The anion or dianion of the compound (I) may be protonated without isolation. For example it may be protonated by reaction with water or dilute aqueous mineral acid (e.g. dilute hydrochloric acid) e.g. an excess of water may be added to the reaction vessel or the reaction mixture may be added to the water. If desired the dianion of the compound in which $R^1$ is hydrogen may be reacted with a (lower) alkylating agent, for example a lower alkyl halide (preferably a lower alkyl iodide), to give an anion of formula (I) in which $R^1$ is lower alkyl. This anion may then be protonated, e.g. by reaction with water.

When $R^3$ and/or $R^4$ is trialkyl-, triaryl- or triarylalkylsilyl the hydrolysis of the product gives a compound of formula I in which R and/or $R^2$ is hydrogen. The hydrolysis may occur during protonation of the anion or dianion of compound (I) by reaction with water.

The lactams of general formula (III) are known compounds or can be prepared by known methods, e.g. by N-"alkylation" of corresponding lactams in which $R^3$ is hydrogen.

EXAMPLE 1

3-Ethylhexahydro-3-(3-methoxyphenyl)-1-methyl-2H-azepin-2-one a solution of butyl lithium (0.05 mole) in hexane (31.25 ml) was treated with 2,2,6,6-tetramethylpiperidine (8.5 ml), followed by dry tetrahydrofuran ("THF"; 100 ml) under an inert atmosphere at 0° C. The mixture was treated with a solution of N-methylcaprolactam (6.25 ml, 50 mM) in THF (20 ml) and stirred for 30 minutes. A solution of butyl lithium (0.05 mole) in hexane (31.25 ml), was added and the mixture stirred for 15 minutes. A solution of o-chloroanisole (6.2 ml) in THF (20 ml) was added slowly, the mixture stirred for 1.5 hours and treated with ethyl iodide (5.15 ml). After one hour, the reaction was quenched with water (100 ml) and the solvents removed under reduced pressure. The residue was partitioned between 2 N HCl (200 ml) and toluene (250 ml). The organic layer was washed with brine, dried and the solvents removed under reduced pressure, to give 3-ethylhexahydro-3-(3-methoxyphenyl)-1-methyl-2H-azepin-2-one (5.5 g) b.p. 140°/0.1 mm. Recrystallisation from diisopropyl ether gave pure title compound (5.0 g) m.p. 68°-69° C., identical with authentic material.

EXAMPLE 2

Hexahydro-3-(3-methoxyphenyl)-1-methyl-2H-azepin-2-one

A solution of butyl lithium (0.05 mole) in hexane (34.4 ml), was treated with 2,2,6,6-tetramethylpiperidine (9.3 ml) followed by dry THF (100 ml) under an inert atmosphere at 0° C. The mixture was treated with N-methylcaprolactam (6.9 ml, 55 mM) and stirred for 30 minutes. A solution of butyl lithium (0.05 mole) in hexane (34.4 ml) was added, the reaction mixture stirred 15 minutes then treated with o-chloroanisole (3.1 ml). After 30 minutes a solution of butyl lithium (0.05 moles) in hexane (31.25 ml) was added, the mixture stirred for 15 minutes and treated with o-chloroanisole (3.1 ml). After a further 30 minutes, the reaction was quenched with water (100 ml) and the solvents removed under reduced pressure. The residue was partitioned between 5 N HCl (100 ml) and toluene (250 ml). The organic phase was washed with brine, dried and the solvents removed under reduced pressure.

Distillation of the residue gave crude title compound (5.4 g) b.p. 150°/0.5 mm. Recrystallisation from diisopropyl ether gave pure material (4.2 g), m.p. 74°-75° C. identical with authentic material.

EXAMPLE 3

Hexahydro-3-(3-methoxyphenyl)-1-methyl-2$\underline{H}$-azepin-2-one

A solution of butyl lithium (0.05 moles) in hexane (31.25 ml), was treated with 2,2,6,6-tetramethylpiperidine (8.5 ml), followed by THF (100 ml) under an inert atmosphere at 0° C. A solution of N-methylcaprolactam (6.25 ml, 50 mM) in THF (20 ml) was added, the mixture stirred for 30 minutes and treated with a solution of butyl lithium (0.05 mole) in hexane (31.25 ml). After 15 minutes, o-chloroanisole (6.2 ml) was added and the mixture stirred for fifteen hours at ambient temperature.

The reaction was quenched with water (100 ml), the solvents removed in vacuo and the residue partitioned beteen 5 N HCl (100 ml) and toluene (250 ml). The organic phase was washed with brine, dried and the solvents removed under reduced pressure. Distillation of the residue gave crude title compound (40%) b.p. about 140°/0.05 mm. Recrystallisation from isopropyl ether gave pure material (31%), m.p. 74°-75° C., identical with authentic material.

EXAMPLE 4

3-Ethylhexahydro-3-(3-methoxyphenyl)-1-methyl-2H-azepin-2-one 2,2,6,6-tetramethylpiperidine (8.48 g) was added dropwise with cooling and stirring under nitrogen to a solution of butyl lithium (0.05 mole) in hexane (31.25 ml) and tetrahydrofuran (15 ml). 3-Ethylhexahydro-1-methyl-2$\underline{H}$-azepin-2-one (7.75 g) in dry tetrahydrofuran (20 ml) was added. On completion of this addition a further portion of butyl lithium (0.06 mole) in hexane (37.5 ml) was added with cooling. After ten minutes o-chloroanisole (8.54 g) was added dropwise in tetrahydrofuran (20 ml). The reaction was then stirred at ambient temperature for c.a. 20 hours. The reaction mixture was poured into water, and the tetrahydrofuran removed under reduced pressure. After acidifying with 5 M hydrochloric acid the mixture was extracted with toluene. Toluene extracts were washed with water, dried (MgSO₄) and after removal of the solvent the product distilled affording 2.37 g, b.p. 150°–170° C. at 0.6 mm. Corrected by purity by g.l.c. assay, the yield of the title compound was 15.8%.

EXAMPLE 5

Hexahydro-3-(3-methoxyphenyl)-2H-azepin-2-one

Hexahydro-1-trimethylsilyl-2H-azepin-2-one (9.2 g) in dry tetrahydrofuran (20 ml) was added dropwise with cooling and stirring under a nitrogen atmosphere to a solution of lithium-2,2,6,6-tetramethylpiperidide (prepared from 2,2,6,6-tetramethylpiperidine (8.48 g) and butyl lithium (0.06 mole) in hexane-tetrahydrofuran (38 ml; 10 ml). A further portion of butyl lithium (0.06 mole) in hexane (38 ml) was then added, followed by o-chloroanisole (8.54 g) keeping the reaction temperature between −10° and 5° C. After allowing to warm to room temperature the reaction was stirred for 1.5 hours then decomposed by the addition of water (100 ml). The solvents were removed under reduced pressure, the resulting product partitioned between toluene and 5 M hydrochloric acid. The toluene extracts were dried (MgSO₄), the solvent removed and the product distilled affording 2.7 g b.p. 160°–170° C. at 0.1 mm, which yielded 2.6 g of the crystalline title compound from ethyl acetate.

EXAMPLE 6

1-Benzylhexahydro-3-(3-methoxyphenyl)2H-azepin-2-one

1-Benzylhexahydro-2H-azepin-2-one (10.2 g) in tetrahydrofuran (100 ml) was added dropwise to a stirred, cooled solution of lithium-2,2,6,6-tetramethylpiperidide [prepared by the addition of 2,2,6,6-tetramethylpiperidine (8.5 g) to butyl lithium (0.05 mole) in hexane (32 ml)] under nitrogen. When the addition was completed a further portion of butyl lithium (0.05 mole) in hexane (32 ml) was added. The solution was cooled to 0° C. and o-chloroanisole (6.2 ml) added dropwise. After stirring at room temperature for four hours the reaction was decomposed with water and the solvents removed under reduced pressure. The resulting oil was partitioned between 5 M hydrochloric acid and toluene. After drying (MgSO₄) the toluene was removed to leave an oil which was distilled affording 5.02 g b.p. 180°–220° C. at 0.2 mm. The oil was crystallised from methanol, affording 3.15 g m.p. 120°–122° C.

Analysis: Found C,77.6; H7.7; N., 4.6. C₂₀H₂₃NO₂; requires C,77.6; H,7.5; N4.5%.

EXAMPLE 7

Hexahydro-3-(3-methoxyphenyl)-1-methyl-2H-azepin-2-one

Diisopropylamine (152 g) in tetrahydrofuran (150 ml) was added over 30 minutes to 15% butyl lithium in hexane (641 g, 1.50 mole) under nitrogen at 20°–25° C. with cooling and the mixture stirred 30 minutes at room temperature. N-methylcaprolactam (63.6 g) in tetrahydrofuran (60 ml) was added over 5 minutes below 25° C. with cooling, the mixture was stirred for one hour at room temperature and then o-chloroanisole (71.3 g) was added over 20 minutes keeping the temperature below 30° C. The reaction mixture was stirred for two hours, water (2. 1.) was added, the product was extracted into ethyl acetate (2×1 1.), the extracts were combined, washed with 2 N hydrochloric acid (1. 1.) and water (500 ml) and evaporated under reduced pressure to give 27.1 g oil.

The crude product was purified by column chromatography by eluting through a basic alumina column with toluene and concentrating the fractions to yield 8.7 g of title compound with melting point 74°–76° C.

EXAMPLE 8

3-(3-Hydroxyphenyl)-1-methyl-2-pyrrolidone

Following the procedure of Example 3, reaction of the lithium anion of 1-methyl-2-pyrrolidone with m-methoxybenzyne (from lithium 2,2,6,6-tetramethylpiperidide and o-chloroanisole) followed by aqueous workup gives 3-(3-methoxyphenyl)-1-methyl-2-pyrrolidone. Removal of the protecting group using iodotrimethylsilane gives the title compound m.p. 113°–4° C. (ethylacetate-hexane).

EXAMPLE 9

3-(3-Hydroxyphenyl)-1-methyl-2-piperidone

Following the procedure of Example 3, reaction of the lithium anion of 1-methyl-2-piperidine with m-benzyloxybenzyne (from lithium 2,2,6,6-tetramethylpiperidide and o-benzyloxychlorobenzene) followed by aqueous work up gives 3-(3-benzyloxyphenyl)-1-methyl-2-piperidone. Removal of the protecting group by hydrogenolysis over palladium on carbon givs the title compound) as the quarter hydrate m.p. 111°–4° C. (hexane).

EXAMPLE 10

Hexahydro-3-(3-hydroxyphenyl)-1-methyl-2H-azepin-2-one

Following the procedure of Example 3, reaction of the lithium anion of N-methylcaprolactam with m-triphenylsiloxybenzyne (from o-chlorotriphenylsilyloxybenzene and lithium tetramethylpiperidide) followed by workup with aqueous acid gives the title compound m.p. 192°–3° C. (ethylacetate).

We claim:

1. A method for preparing a 2-oxo-hexahydroazepine, 2-oxo-piperidine or 2-oxo-pyrrolidine of formula I

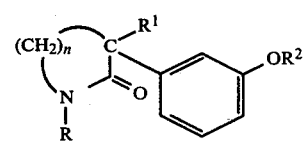

wherein n is 2, 3 or 4, R is selected from the group consisting of hydrogen, lower alkyl, phenyl(lower)alkyl, loweralkenylmethyl and cycloalkylmethyl of 3–4 carbons in the cycloalkyl moiety, R¹ is selected from the group consisting of hydrogen and lower alkyl and R² is selected from the group consisting of hydrogen, lower alkyl and phenyl (lower)alkyl which comprises reacting an anion of a lactam of formula III

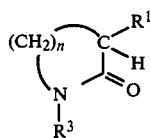

where n and $R^1$ are as defined above and $R^3$ is lower alkyl, phenyl(lower)alkyl, trialkyl-, triaryl- or triaryalkylsilyl, loweralkenylmethyl or cycloalkylmethyl of 3-4 carbon atoms in the cycloalkyl moiety with a benzyne of formula IV

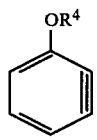

where $R^4$ is lower alkyl, phenyl(lower)alkyl, or trialkyl-, triaryl or triarylalkyl-silyl to give an anion of the compound of formula I where $R^1$ is lower alkyl or a dianion of the compound of formula I where $R^1$ is hydrogen and protonating the anion or dianion of the compound of formula I to give a compound of formula I.

2. A method as claimed in claim 1 wherein the anion of the lactam of formula III is formed in in situ by reacting the lactam of formula III with an alkyl lithium or with a compound of formula MA where M is sodium potassium or lithium and A is selected from diethylamine, diisopropylamine, di-t-butylamine, dicyclohexylamine, t-butylcyclohexylamine, N-t-amyl-N-t-butylamine, N-isopropyl-N-cyclohexylamine, N-(1'-ethylcyclohexyl)-N-1,1,3,3-tetramethylbutylamine, piperidine or 2,2,6,6-tetramethylpiperidine.

3. A method as claimed in claim 1 wherein the benzyne of formula (IV) is formed in situ by reacting a halobenzene of formula (V)

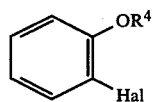

where $R^4$ is as defined in claim 1 and Hal is chlorine, bromine or iodine with a strong base.

4. A method as claimed in claim 1 wherein the anion or dianion of the compound of formula (I) is protonated in situ by reaction with water or dilute aqueous mineral acid.

5. A method of preparing a 2-oxo-hexahydroazepine, 2-oxo-piperidine or 2-oxo-pyrrolidine of formula I

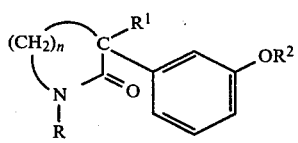

wherein n is 2, 3 or 4, R is selected from the group consisting of hydrogen, lower alkyl, phenyl(lower)alkyl, loweralkenylmethyl and cycloalkylmethyl of 3-4 carbons in the cycloalkyl moiety, $R^1$ is lower alkyl and $R^2$ is selected from the group consisting of hydrogen, lower alkyl and phenyl(lower)alkyl which comprises reacting an anion of a lactam of formula

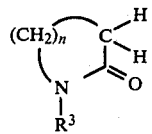

where n is as defined above and $R^3$ is lower alkyl, phenyl(lower)alkyl, trialkyl-, triaryl- or triaryalkylsilyl, loweralkenymethyl or cycloalkylmethyl of 3-4 carbon atoms in the cycloalkyl moiety with a benzyne of formula IV OR$^4$ [benzyne]

where $R^4$ is lower alkyl, phenyl(lower)alkyl, or trialkyl-, triaryl- or triarylalkyl-silyl, reacting the resulting dianion with a (lower)alkylating agent to give an anion of the compound of formula I and protonating the anion of the compound of formula I to give a compound of formula I.

6. A method as claimed in claim 5 wherein the anion of the lactam of formula III is formed in in situ by reacting the lactam of formula III with an alkyl lithium or with a compound of formula MA where M is sodium potassium or lithium and A is selected from diethylamine, diisopropylamine, di-t-butylamine, dicyclohexylamine, t-butylcyclohexylamine, N-t-amyl-N-t-butylamine, N-isopropyl-N-cyclohexylamine, N-(1'-ethylcyclohexyl)-N-1,1,3,3-tetramethylbutylamine, piperidine or 2,2,6,6-tetramethylpiperidine.

7. A method as claimed in claim 5 wherein the benzyne of formula (IV) is formed in situ by reacting a halobenzene of formula (V)

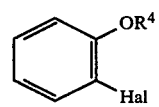

where $R^4$ is as defined in claim 5 and Hal is chlorine, bromine or iodine with a strong base.

8. A method as claimed in claim 5 wherein the anion or dianion of the compound of formula (I) is protonated in situ by reaction with water or dilute aqueous mineral acid.

9. A method for the preparation of a 2-oxo-hexahydroazepine, 2-oxo-piperidine or 2-oxo-pyrrolidine of formula I

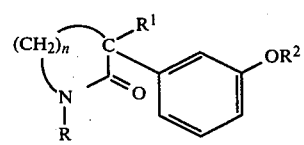

wherein n is 2, 3 or 4, R is selected from the group consisting of hydrogen, lower alkyl, phenyl(lower)alkyl, loweralkenylmethyl and cycloalkylmethyl of 3-4 carbons in the cycloalkyl moiety, $R^1$ is lower alkyl and $R^2$ is selected from the group consisting of hydrogen, lower alkyl and phenyl(lower)alkyl which comprises reacting a lactam of formula

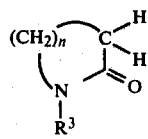

where n is as defined above and $R^3$ is lower alkyl, phenyl(lower)alkyl, trialkyl-, triaryl- or triarylalkylsilyl, loweralkenylmethyl or cycloalkylmethyl of 3-4 carbon atoms in the cycloalkyl moiety with a strong base to form the anion of the lactam in situ, reacting a halobenzene of the formula

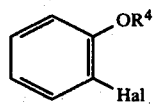

where $R^4$ is lower alkyl, phenyl(lower)alkyl or trialkyl-, triaryl or triaryl-alkyl-silyl and Hal is chlorine, bromine or iodine, with a strong base to form in situ a benzyne of formula

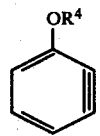

where $R^4$ is as defined above, reacting the anion of the lactam with the benzyne in situ to form a dianion of a compound of formula I where $R^1$ is hydrogen, lower alkylating said dianion to give a dianion of the compound of formula I in which $R^1$ is lower alkyl and protonating the dianion of the compound of formula I in which $R^1$ is lower alkyl to give the compound of formula I.

10. A method as claimed in claim 9 in which the base is lithium 2,2,6,6-tetramethylpiperidide.

11. A method as claimed in claim 9 in which n is 4, R is methyl and $R^1$ is ethyl.

12. A method as claimed in claim 1 in which the product of formula (I) in which $R^1$ is lower alkyl is reduced to a compound of formula

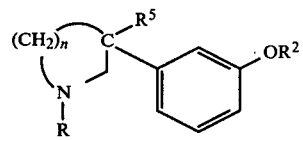

where n, R and $R^2$ are as defined in claim 1 and $R^5$ is lower alkyl.

13. A method as claimed in claim 12 wherein n is 4, R is methyl and $R^5$ is ethyl.

14. A method as claimed in claim 5 in which the product of formula (I) is reduced to a compound of formula

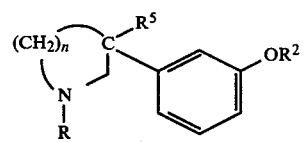

where n, R and $R^2$ are as defined in claim 5 and $R^5$ is lower alkyl.

15. A method as claimed in claim 14 wherein n is 4, R is methyl and $R^5$ is ethyl.

* * * * *